May 29, 1973 C. A. SKIMINA Plant Pat. 3,344
PYRACANTHA PLANT
Filed July 7, 1971
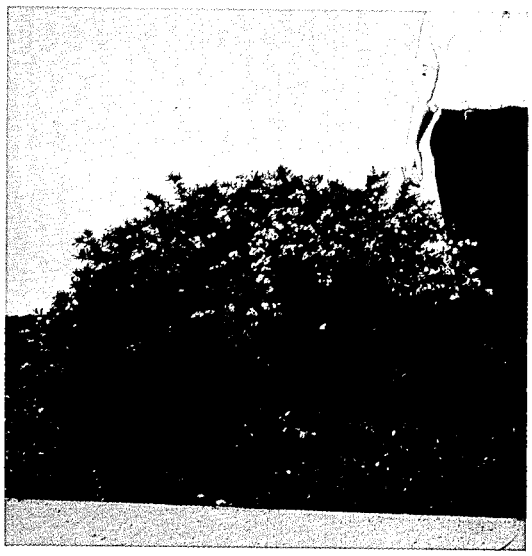
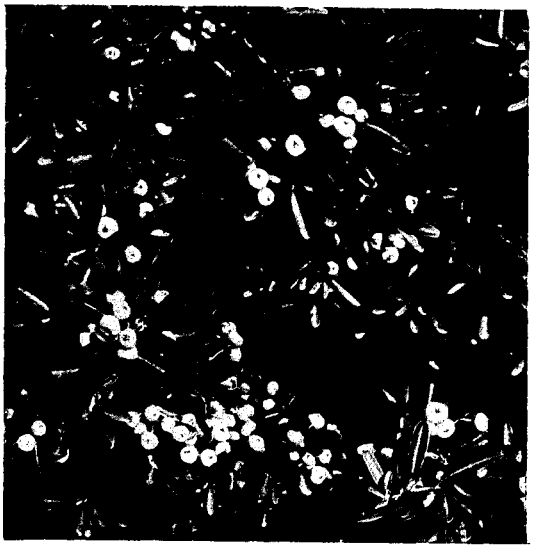

United States Patent Office

Plant Pat. 3,344
Patented May 29, 1973

3,344

PYRACANTHA PLANT

Conrad Andrew Skimina, Claremont, Calif., assignor to Monrovia Nursery Company, Azusa, Calif.

Filed July 7, 1971, Ser. No. 160,575
Int. Cl. A01h *5/00*
U.S. Cl. Plt.—54 1 Claim

ABSTRACT OF THE DISCLOSURE

A new variety of pyracantha plant is disclosed characterized by its pink flowers, red fruit, an extremely prostrate habit, and its ability to survive complete winter periods as low as Zone 4b (−20° F.) on the Plant Hardiness Zone Chart of the U.S. National Arboretum.

The present invention relates to a new and distinct variety of pyracantha plant originated by me by pollinating an unpatented variety of *Pyracantha koidzumi* "Victory" with an unpatented variety of *Crataegus mordanensis* "Toba."

At the time of my invention, it was a primary objective to develop a variety of red-fruited pyracantha plant having pink flowers and a spreading habit of growth that would be hardy below Plant Hardiness Zone 6 as set forth in the Plant Hardiness Zone Chart of the U.S. National Arboretum. Particularly, it was an objective of the invention to develop a variety of pyracantha that would be hardy to expected minimum temperatures of −10° F. to 0° F.

The new variety of pyracantha plant is characterized by its pale pink flower buds and mature flowers mostly white with occasional very pale pink and red fruit and its extremely prostrate habit. The physical appearance of the leaves, flowers and fruit is quite similar to the parent pyracantha plant and the results of cold testing for hardiness reveals that the new variety can survive through complete winter periods as low as Zone 7 (10° F.). The hardiness exhibited by the new variety far exceeds that of its pyracantha parent.

In the accompanying drawing, the upper illustration shows a side elevation view of a typical specimen plant in flower, depicted in color, and the lower illustration shows a view of part of the same plant, bearing its fruit, depicted in color.

The following is a detailed description of my new pyracantha variety with color terminology in accordance with the Royal Horticultural Colour Charts:

A new variety of pyracantha plant was originated by pollinating *Pyracantha koidzumi* "Victory" with *Crataegus mordanensis* "Toba," at Azusa, Calif. The *Pyracantha koidzumi* "Victory" is a variety of pyracantha having large red fruit and white flowers which is hardy to Zone 6b. *Crataegus mordanensis* "Toba" is a hybrid Crataegus from Canada which is extremely hardy and whose flowers are pinkish.

The plant has been asexually reproduced at Azusa, Calif.

The new variety of pyracantha plant exhibits a very low dense habit. Five year old plants are about 30 inches in height with a spread of 120 inches. Growth is very vigorous.

Foliage: The leaves are alternate, simple, and of good substance, being about ¾ inch to 1 1/16 inch long and about 5/16 inch to ⅜ inch wide. The younger foliage is oblanceolate to oblong, with the upper surfaces Parsley Green, 00962 in color. The older leaves are elliptic with the upper surfaces Ivy Green, 0001060/2. Both types of leaves are retuse at the apex while the bases are attenuate, rarely obtuse. The undersides of both types of leaves are Spinach Green in color, 0960/3. The margins of the leaves are sparsely serrate to entire.

Fruit: The fruit is pomaceous, measuring about ¼ inch to 5/16 inch across and about 3/16 inch in height. The fruit is borne in very large clusters, and each contains about five seeds. The fruit ripens in early to mid-summer and exhibits the color of Capsicum Red, 715/2. The fruit generally remains on the branches until late fall or early winter.

Flowers: The flowers are single. When the flower buds first break they appear pink, but mature flowers are white to an occasional very pale pink (Dawn Pink 523/3), measuring about ⅜ inch in diameter. The flowers appear in massive clusters and generally blossom in early to mid-spring. They are of regular structure with five petals, numerous stamens, and five fused pistils. The flower clusters are generally borne on one-year wood.

Branches: The first year wood is reddish brown in color with a spattering of fine pubescence along the internodes. The older branches are grayish-brown with a glaucous bloom. Thorns, generally measuring about ½ inch in length, are present along the branches. The older wood tends to be brittle.

Hardiness: The new variety of pyracantha plant is quite hardy and can survive through complete winter periods as low as Zone 7, temperatures as low as −10° F.

What is claimed is:

1. A new and distinct variety of white flowered with occasional pale pink or pinkish cast and red-fruited pyracantha plant, substantially as herein shown and described, characterized particularly as to novelty by its extremely prostrate habit and its hardiness to survive through complete winter periods as low as Zone 7 of the Plant Hardiness Zone Chart of the U.S. National Arboretum.

No references cited.

ROBERT E. BAGWILL, Primary Examiner

PO-1070
(5/69)

UNITED STATES PATENT OFFICE
CERTIFICATE OF CORRECTION

Patent No. Plant 3344 Dated May 29, 1973

Inventor(s) CONRAD ANDREW SKIMINA

It is certified that error appears in the above-identified patent and that said Letters Patent are hereby corrected as shown below:

Column 1, line 14

"Zone 4b(-20°F.) should read --Zone 7(+10°F.)--

Column 2, line 13

"00962" should read --oo962--

Column 2, line 14

"0001060/2" should read --ooo1060/2--

Column 2, line 17

"0960/3" should read --o960/3--

Column 2, line 42

"-10° F." should read -- +10° F.--

Signed and sealed this 5th day of February 1974.

(SEAL)
Attest:

EDWARD M.FLETCHER,JR.
Attesting Officer

RENE D. TEGTMEYER
Acting Commissioner of Patents